US006117858A

United States Patent [19]
Porter et al.

[11] Patent Number: 6,117,858
[45] Date of Patent: Sep. 12, 2000

[54] COMPOSITIONS AND METHODS FOR ALTERING THE BIODISTRIBUTION OF BIOLOGICAL AGENTS

[75] Inventors: Thomas R. Porter, Omaha, Nebr.; Patrick L. Iversen, Corvallis, Oreg.

[73] Assignee: The Board of Regents of the University of Nebraska, Lincoln, Nebr.

[21] Appl. No.: 09/118,168

[22] Filed: Jul. 17, 1998

Related U.S. Application Data

[63] Continuation-in-part of application No. 08/670,999, Jun. 28, 1996, Pat. No. 5,849,727.

[51] Int. Cl.[7] ..... A01N 51/00

[52] U.S. Cl. ..... 514/156; 424/9.52

[58] Field of Search ..... 424/9.5, 9.52, 424/9; 514/44, 156

[56] References Cited

U.S. PATENT DOCUMENTS

| | | | |
|---|---|---|---|
| 4,572,203 | 2/1986 | Feinstein | 600/443 |
| 4,634,586 | 1/1987 | Goodwin et al. | 424/1.65 |
| 4,718,433 | 1/1988 | Feinstein | 424/9.52 |
| 4,774,958 | 10/1988 | Feinstein | 600/350 |
| 4,844,882 | 7/1989 | Widder et al. | 424/9.52 |
| 4,957,656 | 9/1990 | Cerny et al. | 424/9.52 |
| 5,040,537 | 8/1991 | Katakura | 600/431 |
| 5,107,842 | 4/1992 | Levene et al. | 424/9.52 |
| 5,255,683 | 10/1993 | Monaghan | 600/458 |
| 5,304,325 | 4/1994 | Kaufman et al. | 516/56 |
| 5,310,540 | 5/1994 | Giddey et al. | 424/9.52 |
| 5,315,997 | 5/1994 | Widder et al. | 600/420 |
| 5,315,998 | 5/1994 | Tachibana et al. | 601/2 |
| 5,380,519 | 1/1995 | Schneider et al. | 600/458 |
| 5,385,147 | 1/1995 | Anderson et al. | 600/458 |
| 5,385,725 | 1/1995 | Lin et al. | 424/9.52 |
| 5,393,524 | 2/1995 | Quay | 424/9.52 |
| 5,401,493 | 3/1995 | Lohrmann et al. | 424/9.3 |
| 5,409,688 | 4/1995 | Quay | 424/9.52 |
| 5,410,516 | 4/1995 | Uhlendorf et al. | 367/7 |
| 5,413,774 | 5/1995 | Schneider et al. | 424/9.51 |
| 5,439,686 | 8/1995 | Desai et al. | 424/451 |
| 5,445,813 | 8/1995 | Schneider et al. | 424/9.51 |
| 5,512,268 | 4/1996 | Grinstaff et al. | 424/9.322 |
| 5,540,909 | 7/1996 | Schutt | 424/9.52 |
| 5,542,935 | 8/1996 | Unger et al. | 604/190 |
| 5,552,133 | 9/1996 | Lambert et al. | 424/9.52 |
| 5,558,853 | 9/1996 | Quay | 424/9.5 |
| 5,560,364 | 10/1996 | Porter | 600/458 |
| 5,567,415 | 10/1996 | Porter | 424/9.52 |
| 5,580,859 | 12/1996 | Felgner et al. | 514/44 |
| 5,585,479 | 12/1996 | Hoke et al. | 536/24.5 |

FOREIGN PATENT DOCUMENTS

| | | |
|---|---|---|
| 0 633 030 A1 | 1/1995 | European Pat. Off. . |
| WO 93/05819 | 4/1993 | WIPO . |
| WO 94/16739 | 8/1994 | WIPO . |
| WO 94/18954 | 9/1994 | WIPO . |
| WO 95/23615 | 9/1995 | WIPO . |

OTHER PUBLICATIONS

Porter et al. Circulation. vol. 92 (9) pp. 2391–2395, Nov. 1995.

Porter et al. J. American College of Cardiology. vol. 25(2) pp. 509–515, Feb. 1995.

Anderson, Editorial, "Gene Therapy for Genetic Diseases", *Human Gene Therapy*, vol. 5, pp. 281–282 (1994), Mary Ann Liebert, Inc., Publishers.

Bleeker, H., "On the Application of Ultrasonic Contrast Agents for Blood Flowmetry and Assessment of Cardiac Perfusion", *Ultrasound Med*, 9:461–471 (1990).

Brown, "New Media, Researchers 'Oversold' Gene Therapy, Advisory Panel Says", The Washington Post (Dec. 8, 1995).

Challita & Kohn, "Lack of Expression from a Retroviral Vector After Transduction of Murine Hematopoietic Stem Cells is Associated with Methylation in vivo", Proc. Natl. Acad. Sci., USA, vol. 91, pp. 2567–2571 (Mar. 1994).

Coghlan, Focus, Editorial, "Gene Dream Fades Away", *New Scientist*, vol. 148, No. 2005, pp. 14–15 (Nov. 25, 1995).

Gura, T., "Antisense Has Growing Pains", *Science*, vol. 270, pp. 575–577 (1995).

Jaroff, "Keys to the Kingdom", *Time*, vol. 148, No. 14, pp. 25–29 (1996).

Kricsfeld, A., "Detection of Regional Perfusion Abnormalities During Adenoosine Stress Echocardiography Using Intravenous Perfluoropropane–enhanced Sonicated Dextrose Albumin", *J. Am. Col. of Card.*, special issue, p. 38A Feb. 1995 (abstract XP000577057).

Marshall, "Gene Therapy's Growing Pains", *Science,* vol. 269, pp. 1050–1055 (Aug. 25, 1995).

Orkin et al., Report and Recommendations of the Panel to Assess the NIH Investment in Research on Gene Therapy (Dec. 7, 1995).

Porter et al., "The Mechanism and Clinical Implication of Improved Left Ventricular Videointensity Following Intravenous Injection of Multi–fold Dilutions of Albumin with Dextrose", *International Journal of Cardiac Imaging*, vol. 11, pp. 117–125 (1995).

Porter et al., "Transient Myocardial Contrast After Initial Exposure to Diagnostic Ultrasound Pressures with Minute Doses of Intravenously Injected Microbubbles: Demonstration and Potential Mechanisms", *Circulation*, vol. 92, No. 9, pp. 2391–2395 (1995).

(List continued on next page.)

*Primary Examiner*—Remy Yucel
*Attorney, Agent, or Firm*—LeeAnn Gorthey; Heidi S. Nebel; Zarley, McKee, Thomte, Voorhees & Sease

[57] ABSTRACT

The invention relates to a new and improved pharmaceutical composition and method for delivery of therapeutic agents. The methods and composition of the invention can be used with several therapeutic agents and can achieve site specific delivery of a therapeutic or diagnostic substance. This can allow for lower doses and for improved efficacy with drugs which traditionally reach targeted sites and can result in improved utility for agents such as oligonucleotides and polynucleotides which are plagued with problems with biodistribution.

9 Claims, 1 Drawing Sheet

OTHER PUBLICATIONS

Porter, T., "Echocardiographic Detection of Residual Coronary Flow Abnormalities and Stenosis Severity After Coronary Reperfusion Using Intravenous Perfluoropropane–enhanced Sonicated Dextrose Albumin", 44th Annual Scientific Session of the American College of Cardiology, New Orleans, LA, USA, Mar. 19–22, 1995. *J. Am. Col. of Card.*, special issue, p. 205AFeb. 1995 (abstract 95–60) XP000577058.

Porter, T., "Multifold Sonicated Dilutions of Albumin with Fifty Percent Dextrose Improve Left Ventricular Contrast Videointensity After Intravenous Injection in Human Beings", *J. Am. Soc. Echocard.*, 7(5) 465–471 (1994).

Porter, T., "Myocardial Contrast Echocardiography for the Assessment of Coronary Blood Flow Reserve: Validation in Humans", *JACC*, 21(2) 349–355 (1993).

Porter, T., "Noninvasive Indentification of Acute Myocardial Ischemia and Reperfusion with Contrast Ultrasound Using Intravenous Perfluoropropane–Exposed Sonicated Dextrose Albumin", *J. Am. Col. of Card.*, 26(1) 33–40 (1995).

Xie, F., "Acute Myocardial Ischemia and Reperfusion can be Visually Identified Non–invasively with Intravenous Perfluoropropane–Enhanced Sonicated Dextrose Albumin Ultrasound Contrast", Abstract From the 67th Scientific Sessions Dallas Convention Center, Dallas TX, Nov. 14–17, 1994, 90(2) Part 2, p. 1555 Oct. 1994 (abstract XP000577054).

Xie, F., "Perfluoropropane enhanced Sonicated Dextrose Albumin Produces Visually Apparent Consistent Myocardial Opecification with Physiologic Washout and Minimal Homodynamic Changes Following... Injection", Abstract From the 67th Scientific Sessions Dallas Convention Center, Dallas TX, Nov. 14–17, 1994, 90(4) Part 2, p. 269 Oct. 1994 (abstract XP000577055).

Fig. 1

COMPOSITIONS AND METHODS FOR ALTERING THE BIODISTRIBUTION OF BIOLOGICAL AGENTS

CROSS-REFERENCE TO RELATED APPLICATION

This application is a continuation-in-part of application Ser. No. 08/670,999, filed Jun. 28, 1996, now U.S. Pat. No. 5,849,727 the disclosure of which is hereby incorporated by reference.

FIELD OF THE INVENTION

This invention relates to a new and improved pharmaceutical composition and method for delivery of bioactive substances. The methods and composition of the invention can be used with several agents and can achieve site specific delivery of a biologically active substances. This can allow for lower doses and for improved efficacy with drugs particularly agents such as oligonucleotides which are plagued with problems in achieving therapeutic concentrations at targeted organs.

BACKGROUND OF THE INVENTION

Drug delivery techniques are employed in the formulation of all drug therapy to augment drug availability, to reduce drug dose, and consequently to reduce drug-induced side effects. These techniques serve to control, regulate, and target the release of drugs in the body. The goals have been to provide less frequent drug administration, to maintain constant and continuous therapeutic levels of a drug in the systemic circulation or at a specific target organ site, to achieve a reduction in undesirable side effects, and to promote a reduction in the amount and dose concentration required to realize the desired therapeutic benefit.

To date, drug delivery systems have included drug carriers based upon proteins, polysaccharides, synthetic polymers, erythrocytes, DNA and liposomes. New generation biologicals such as monoclonal antibodies, gene therapy vectors, anti-cancer drugs such as Taxol, viral based drugs, and oligo and poly nucleotides have presented several problems with regard to delivery. In fact drug delivery may be the primary hurdle to achieving mainstream therapeutic use of these biologics whose initial potential seemed unlimited but whose therapeutic parameters have prevented realization of full benefit.

Synthetic oligodeoxyribonucleotides which are chemically modified to confer nuclease resistance represent a fundamentally different approach to drug therapy. The most common applications to date are antisense oligos with sequences complementary to a specific targeted mRNA sequence. An antisense oligonucleotide approach to therapy involves a remarkably simple and specific drug design concept in which the oligo causes a mechanistic intervention in the processes of translation or an earlier processing event. The advantage of this approach is the potential for gene-specific actions which should be reflected in a relatively low dose and minimal non-targeted side effects.

Phosphorothioate analogs of polynucleotides have chiral internucleoside linkages in which one of the non-bridging ligands is sulfur. The phosphorothioate analog is currently the most commonly employed analogue in biological studies including both in vitro and in vivo. The most apparent disadvantage of phosphorothioate oligonucleotides include the high cost of preparation of sufficient amounts of high quality material and non-specific binding to proteins. Hence, the primary advantage of antisense approach (low dose and minimal side effects) fall short of expectations.

Drug delivery efforts with regard to oligonucleotides and polynucleotides have focused on two key challenges; transfection of oligonucleotides into cells and alteration of distribution of oligonucleotides in vivo.

Transfection involves the enhancement of in vitro cellular uptake. Biological approaches to improve uptake have included viral vectors such as reconstituted viruses and pseudo virions, and chemicals such as liposomes. Methods to improve biodistribution have focused on such things as cationic lipids, which are postulated to increase cellular uptake of drugs due to the positively charged lipid attraction to the negatively charged surfaces of most cells.

Lipofection and DC-cholesterol liposomes have been reported to enhance gene transfer into vascular cells in vivo when administered by catheter. Cationic lipid DNA complexes have also been reported to result in effective gene transfer into mouse lungs after intratracheal administration.

Cationic liposomal delivery of oligonucleotides has also been accomplished however, altered distribution to the lung and liver was experienced. Asialoglycoprotein poly(L)-lysine complexes have met with limited success as well as complexation with Sendai virus coat protein containing liposomes. Toxicity and biodistribution, however, have remained significant issues.

From the foregoing it can be seen that a targeted drug delivery system for delivery of biologics, particularly poly and oligo nucleotides is needed for these drugs to achieve their fullest potential.

One object of this invention is to provide a novel composition of matter to deliver a pharmaceutical agent to a targeted site in vivo.

Another object of the invention is to provide a method for delivering a pharmaceutical agent, increasing drug bioavailability and decreasing toxicity.

Another object of the invention is to provide a method of forming a novel composition of matter for delivering a pharmaceutical agent to a targeted site in vivo by sonicating perfluorocarbon containing microbubbles in a nitrogen-free environment.

Other objects of the inventions will become apparent from the description of the invention which follows.

SUMMARY OF THE INVENTION

According to the invention a new biologically active agent delivery method and composition are disclosed. The compositions and methods can be used to deliver agents such as therapeutics or diagnostics which have been plagued with delivery problems, such as oligonucleotides, as well as traditional agents and can drastically reduce the effective dosages of each, increasing the therapeutic index and improving bioavailability. This in turn can reduce drug cytotoxicity and side effects.

The invention employs conjugation of the biologic agent with a filmogenic protein which is formed as a protein shell microbubble encapsulating an insoluble gas. The composition is prepared as an aqueous suspension of a plurality of the microbubbles for parenteral administration. Conjugation of the biologic with albumin or other such protein encapsulated microbubbles can allow for targeted delivery of the biologic to alternate including those which traditionally interact with the protein.

Improved gas-filled microbubbles with enhanced stability and thus better delivery capabilities are achieved by forming the microbubbles in the presence of a nitrogen-free environment. The nitrogen-free environment makes microbubbles which are significantly smaller than microbubbles obtained in a room air environment. These smaller microbubbles are more stable than microbubbles manufactured in a room air environment and result in improved delivery of the biologic.

DESCRIPTION OF THE FIGURES

FIG. 1 is a Lineweaver-Burke plot of the binding data for PESDA microbubbles with PS-ODN. The equilibrium dissociation constant $K_m$ (calculated for the 7 concentrations which were run in duplicate) for the binding to the microbubbles was $1.76 \times 10^{-5}$M. ($r^2$=0.999; Y–int=0.0566; 7 concentrations). This is nearly within the range observed for binding a 15mer PS-ODN with sequence 5'd (AACGTTGAGGGGCAT)-3' (SEQ ID NO:1) to human serum albumin in solution of 3.7–4.8x10–5M previously reported Srinivasan SK et al, "Characterization of binding sites, extent of binding, and drug interactions of oligonucleotides with albumin. Antisen Res. Dev. 5:131, 1995.

DETAILED DESCRIPTION OF THE INVENTION

Ultrasonic imaging has long been used as a diagnostic tool to aid in therapeutic procedures. It is based on the principle that waves of sound energy can be focused upon an area of interest and reflected to produce an image. Generally an ultrasonic transducer is placed on a body surface overlying the area to be imaged and ultrasonic energy, produced by generating and receiving sound waves, is transmitted. The ultrasonic energy is reflected back to the transducer where it is translated into an ultrasonic image. The amount of characteristics of the reflected energy depend upon the acoustic properties of the tissues, and contrast agents which are echogenic are preferably used to create ultrasonic energy in the area of interest and improve the imaging received. For a discussion of contrast echographic instrumentation, see, DeJong and, "Acoustic Properties of Ultrasound Contrast Agents", CIP-GEGEVENS KONINKLIJKE BIBLIOTHEEK, DENHAG (1993), pp. 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

Ultrasonic vibration has also been used at therapeutic levels in the medical field to increase the absorption of various medicaments. For example in Japanese Patent Kokai number 115591/1977 discloses that percutaneous absorption of a medicament is enhanced by ultrasonic vibration. U.S. Pat. Nos. 4,953,565 and 5,007,438 also disclose a technique of percutaneous absorption of medicaments by the aid of ultrasonic vibration. U.S. Pat. No. 5,315,998 discloses a booster for drug therapy comprising microbubbles in combination ultrasonic energy to allow the medicament to diffuse and penetrate. This discloses the use of therapeutic levels of ultrasound for up to 20 minutes in contrast to the invention which uses diagnostic levels of ultrasound with exposure for much shorter time periods to achieve release of conjugated bioactive agents.

Applicant has demonstrated that traditional diagnostic ultrasound therapy contrast agents can be used as a specific targeted delivery device to release therapeutic agents at the specifically designated sites of interest thereby altering drug distribution. Surprisingly, this objective can be accomplished with the contrast agent alone and without the use of any diagnostic ultrasound.

The pharmaceutical composition of the invention comprises a liquid suspension containing microbubbles of an insoluble gas having a diameter of 0.1 to 10 microns. The microbubbles are formed by entrapping microbubbles of a gas into a liquid. The microbubbles are made of various insoluble gases such as fluorocarbon or sulfur hexafluoride gas. The liquid includes any liquid which can form microbubbles. Generally any insoluble gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, perfluoropentane are preferred. Of these gases, perfluoropropane and perfluorobutane are especially preferred because of their demonstrated safety for intraocular injection in humans. They have been used in human studies for intraocular injections to stabilize retinal detachments (Wong and Thompson, Opthamology 95:609–613). Treatment with intraocular perfluoropropane is considered to be the standard of care for treatment of this disorder. The gases must also have a diffusion coefficient and blood solubility lower than nitrogen or oxygen which diffuse once in the internal atmosphere of the blood vessel.

Other inert gases such as sulfur hexafluoride are also useful in the invention provided they have a diffusion coefficient and blood solubility lower than nitrogen or oxygen. The agent of the invention is formulated in a pharmaceutically effective dosage form for peripheral administration to the host. Generally such host is a human host, although other mammalian hosts such as canine or equine can also be subject to this therapy.

The pharmaceutical liquid composition of the invention uses a liquid wherein the microbubbles are stabilized by a filmogenic protein coating. Suitable proteins include naturally occurring proteins such as albumin, human gamma globulin, human apotransferin, Beta lactose and urease. The invention preferably employs a naturally occurring protein but synthetic proteins may also be used. Preferred is human serum albumin.

It is also optional to use an aqueous solution containing a mixture of a pharmaceutically accepted saccharide e.g., dextrose, in combination with the earlier described protein. In a preferred embodiment the pharmaceutical liquid composition of the invention is the sonicated mixture of commercially available albumin (human), U.S.P. solution (generally supplied as 5% or 25% by weight sterile aqueous solutions), and commercially available dextrose, U.S.P. for intravenous administration. The mixture is sonicated under ambient conditions i.e. room air temperature and pressure and is perfused with an insoluble gas (99.9% by weight) during sonication.

In a most preferred embodiment the pharmaceutical liquid composition includes a two-fold to eight-fold dilution of 5% to 50% by weight of dextrose and a 2% to 10% by weight of human serum albumin. Exemplary of other saccharide solutions of the invention are aqueous monosaccharide solution (e.g. having the formula $C_6H_{12}O_6$ such as the hexose sugars, dextrose or fructose or mixtures thereof), aqueous disaccharide solution (e.g. having a formula $C_{12}H_{22}O_{11}$ such as sucrose, lactose or maltose or mixtures thereof), or aqueous polysaccharide solution (e.g. soluble starches having the formula $C_6H_{10}O_5(n)$ wherein n is a whole number integer between 20 and about 200 such as amylase or dextran or mixtures thereof.

The microbubbles are formed by sonication, typically with a sonicating horn. Sonication by ultrasonic energy causes cavitation within the dextrose albumin solution at sites of particulate matter or gas in the fluid. These cavitation sites eventually resonate and produce small microbubbles (about 7 microns in size) which are non-collapsing and stable. In general, sonication conditions which produce concentrations of greater than about $4 \times 10^8$ m of between about 5 and about 6 micron microbubbles are preferred. Generally the mixture will be sonicated for about 80 seconds, while being perfused with an insoluble gas, in the presence of room air.

A second method of preparation includes hand agitating 15±2 ml of sonicated dextrose albumin with 8±2 ml of perfluorocarbon gas prior to sonication. Sonication then proceeds for 80±5 seconds.

In a preferred embodiment, the microbubbles are formed in a 100% oxygen or a nitrogen-free environment. Microbubbles formed in these environments are significantly smaller than those formed in the presence of room air. These smaller microbubbles are more stable and result in improved delivery of biologics.

The inventors became aware of the advantages of using a nitrogen-free environment or 100% oxygen through the observation that gas-filled microbubbles produced better ultrasound contrast following venous injection than room air filled microbubbles. One reason for this improved contrast is the prolonged survival of the gas-filled microbubbles following intravenous injection. In comparison, room air filled microbubbles of comparable size are rapidly destroyed following venous injection because of rapid diffusion of the soluble gases out of the microbubble. Computer simulations, however, have shown that these soluble gases still affect the size of gas-filled microbubbles in blood, thereby affecting their ultrasound characteristics. Burkard, M. E. et al. (1994), Oxygen transport to tissue by persistent bubbles: theory and simulations. J Appl Physiol 2874–8. These models have theorized that blood nitrogen plays an important role in preventing the outward diffusion of the gas within the microbubble.

It was postulated that by enhancing microbubble oxygen content (thus lowering partial pressures of nitrogen within the microbubble), they could prolong microbubble survival in blood. The presence of a nitrogen-free environment was found to produce substantially smaller microbubbles which are more stable in the bloodstream. This results in improved contrast and drug delivery.

These microbubble sizes are particularly ideal since a microbubble must have a mean diameter of less than 10 microns and greater than 0.1 to be sufficient for transpulmonary passage, and must be stable enough to prevent significant diffusion of gases within the microbubble following intravenous injection and during transit to the target site.

As used herein the term "nitrogen free" shall mean a nitrogen content which is less than that of room air such that the partial pressure of nitrogen in gas-filled microbubbles formed by sonication is lower than that achieved from sonication with room air (typically about 70–80% nitrogen).

The microbubbles are next incubated with the medicament so that the medicament becomes conjugated with the microbubble. Quite unexpectedly it was demonstrated that filmogenic proteins in the form of microbubbles as previously used in contrast agents retain their ability to bind medicaments. This is surprising because traditionally it was thought that in the formation of microbubble contrast agents the protein sphere was made of denatured protein. Applicant has demonstrated that when an insoluble gas instead of air is used for the microbubble, much of the sonication energy is absorbed by the gas and the protein retains its binding activity. Air filled microbubbles do not retain their binding capabilities and cannot be used in the method of the invention.

The therapy involves the use of a pharmaceutical composition conjugated to a protein microbubble of a diameter of about 0.1 to 10 microns. The invention uses agents traditionally used in diagnostic ultrasound imaging.

Therapeutic agents useful in the present invention are selected via their ability to bind with the filmogenic protein. For example if the filmogenic protein is albumin, the therapeutic or diagnostic agent can include oligonucleotides (such as antisense or antigen oligos), polynucleotides (such as retroviral, adenoviral, plasmid vectors or probes), or ribozymes all of which can bind with albumin and as such can form a conjugation with the microbubble. A list of drugs which bind to albumin at site 1 (which retains its binding capacity) and thus would be useful in the methods and compositions of the present invention in the albumin embodiment follows:

| Drug | % Albumin Binding | Drug Class |
| --- | --- | --- |
| Naproxen | 99.7 | NSAID⊕ |
| Piroxicam | 99.3 | NSAID⊕ |
| Warfarin | 99.0 | Anticoagulant |
| Furosemide | 98.8 | Loop diuretic |
| Phenylbutazone | 96.1 | NSAID⊕ |
| Valproic Acid | 93.0 | Antiepileptic |
| Sulfisoxazole | 91.4 | Sulfonimide Antibiotic |
| Ceftriaxone | 90–95* | Third Generation cephalosporin antibiotic |
| Miconazole | 90.7–93.1* | Antifungal |
| Phenytoin | 89.0 | Antiepileptic |

⊕Nonsteroidal anti inflammatory drug
*Represents patient-to-patient variability

Other drugs which bind with albumin particularly at site 1 would also be useful in this embodiment and can be ascertained by those of skill in the art through Drug Interaction and Pharmacology tests standard to those of skill in the art such as "Drug Information or "Facts and Comparisons" published by Berney Olin updated every quarter. Other such references are widely available in the art. Assays for determination of appropriate protein-therapeutic combinations are disclosed herein and can be used to test any combination for its ability to work with the method of the invention.

According to a preferred embodiment of the invention, protein coated microbubbles of insoluble gas have been found to form stable conjugates with oligonucleotides. The oligo conjugated bubbles are then introduced to the animal and the protein coating directs the conjugated agent to sites of interaction. Ultimately as the bubble dissipates the agent will be released at the tissue site.

This is of particular relevance to oligonucleotide and polynucleotide therapy as the primary hurdle to effective anti-sense, anti-gene, or even gene therapy employing viral or plasmid nucleotide delivery is the ability of the therapeutic to reach the target site at high enough concentrations to achieve a therapeutic effect. Therapeutic sites can include such things as the location of a specific tumor, an organ which due to differential gene activation expresses a particular gene product, the site of an injury or thrombosis, a site for further processing and distribution of the therapeutic etc. Generally the target site is selected based upon the bioprocessing of the filmogenic protein. For example the kidneys and liver take up albumin and albumin microbubbles can be used to specifically direct the administration of conjugated bioactive agents to these areas. The metabolism and bioprocessing of other filmogenic proteins can be easily obtained through standard pharmacologic texts such as "Basic and Clinical Pharmacology" by Bertram G. Katzung the relevant disclosure of which is incorporated by reference.

The method preferred for practicing the delivery therapy of the invention involves obtaining a pharmaceutical liquid agent of the invention, introducing said agent into a host by intravenous injection, intravenously (i.v. infusion), percutaneously or intramuscularly. The microbubble is then processed in the animal and is taken up and interacted with according to the filmogenic protein which coats the microbubble. Ultimately the bubble dissipates delivering the bioactive at the site of processing of the protein.

It has been previously shown by applicants that microbubble conjugation of bioactive agents can be used in targeted delivery protocols with delivery of the biologic upon application of ultrasound to the target site, causing cavitation of the microbubble and ultimate release of the biologic at the site in interaction with the ultrasound field. Quite unexpectedly, applicant has now discovered that application of ultrasound is not necessary for the targeted delivery of biologics to sites of bioprocessing of the protein coating. The protein traffics the microbubble and conjugate to sites of processing and as the bubbles dissipate the oligo or other biologic is released to interact with the site allowing for a fraction of the biologic to achieve the same biological effect.

In a preferred embodiment the agent of the invention is a perfluorocarbon enhanced sonicated dextrose albumin solution comprised of a sonicated three-fold dilution of 5% human serum albumin with 5% dextrose. During sonication, the solution is perfused with perfluorocarbon gas for about 80 seconds which lowers the solubility and diffusivity of the microbubble gas. The resulting microbubbles are concentrated at room temperature for at least about 120±5 minutes wherein the excess solution settles in the sonicating syringe. The microbubbles are then exposed to a therapeutic agent and allowed to interact such that the agent becomes conjugated to the microbubbles. Next the conjugated microbubbles are transferred to a sterile syringe and injected parenterally into a mammal, preferably near the target site of activity of the agent.

Methods of ultrasonic imaging in which microbubbles formed by sonicating an aqueous protein solution are injected into a mammal to alter the acoustic properties of a predetermined area which is then ultrasonically scanned to obtain an image for use in medical procedures is well known. For example see U.S. Pat. No. 4,572,203, U.S. Pat. No. 4,718,433 and U.S. Pat. No. 4,774,958, the contents of each of which are incorporated herein by reference.

It is the use of these types of contrast agents as a pharmaceutical composition as part of a targeted delivery system that is the novel improvement of this invention. The use of a nitrogen-free environment in the manufacture of the contrast agents is also a novel improvement in the effectiveness of the contrast agent in myocardial imaging.

The invention has been shown to drastically improve the efficiency and therapeutic activity by altering biodistribution of several drugs including, most notably, anti-sense oligonucleotides which have been traditionally plagued with ineffective pharmacologic parameters, including high clearance rate and toxicity.

This is particularly significant as the microbubble-therapeutic agent therapy can reduce any toxic effects of persons who perhaps could not tolerate certain therapeutics at doses and concentrations necessary to achieve a beneficial result.

The protein substance such as human serum albumin is easily metabolized within the body and excreted outside and hence is not harmful to the human body. Further gas trapped within the microbubbles is extremely small and is easily dissolved in blood fluid, perfluoropropane and perfluorobutane have long been known to be safe in humans. Both have been used in humans for intra ocular injections to stabilize retinal detachments. Wong and Thompson, ophthalmology 95:609–613. Thus the anti thrombosis agents of the invention are extremely safe and nontoxic for patients.

The invention is particularly useful for delivery of nucleotide sequences in the form of gene therapy vectors, or anti-sense of anti-gene type strategies to ultimately alter gene expressions in target cells.

Antisense oligonucleotides represent potential tools in research and therapy by virtue of their ability to specifically inhibit synthesis of target proteins. A major theoretical advantage of these oligos is their potential specificity for binding to one site in the cell. According to one embodiment of the invention a synthetic oligonucleotide of at least 6 nucleotides, preferably complementary to DNA (antigene) or RNA (antisense), which interferes with the process of transcription or translation of endogenous proteins is presented.

Any of the known methods for oligonucleotide synthesis can be used to prepare the oligonucleotides. They are most conveniently prepared using any of the commercially available, automated nucleic acid synthesizers, such as applied biosystems, Inc., DNA synthesizer (Model 380B). According to manufacturers protocols using phosphoroamidite chemistry. After biosystems (Foster City, Calif.). Phosphorothioate oligonucleotides were synthesized and purified according to the methods described in Stek and Zahn J. Chromatography, 326:263–280 and in Applied Biosystems, DNA Synthesizer, User Bulletin, Models 380A-380B-381A-391-EP, December 1989. The oligo is introduced to cells by methods which are known to those of skill in the art. See Iverson, et al., "Anti-Cancer Drug Design", 1991, 6531–6538, incorporated herein by reference.

Traditional limitations of oligonucleotide therapy have been preparation of the oligonucleotide analogue which is substantially resistant to the endo and exonucleases found in the blood and cells of the body. While unmodified oligos have been shown to be effective, several modifications to these oligos has helped alleviate this problem.

Modified or related nucleotides of the present invention can include one or more modifications of the nucleic acid bases, sugar moieties, internucleoside phosphate linkages, or combinations of modifications at these sites. The internucleoside phosphate linkages can be phosphorothioate, phosphoramidate; methylphosphonate, phosphorodithioate and combinations of such similar linkages (to produce mix backbone modified oligonucleotides). Modifications may be internal or at the end(s) of the oligonucleotide molecule and can include additions to the molecule of the internucleoside phosphate linkages, such as cholesterol, diamine compounds with varying numbers of carbon residues between the amino groups, and terminal ribose, deoxyriboase and phosphate modifications which cleave, or crosslink to the opposite chains or to associated enzymes or other proteins which bind to the genome.

These modifications traditionally help shield the oligo from enzymatic degradation within the cell. Any of the above modifications can be used with the method of the invention. However, in preferred embodiment the modification is a phosphorothioate oligonucleotide.

The following examples are for illustration purposes only and are not intended to limit this invention in any way. It will be appreciated by those of skill in the art, that numerous other protein-bioactive agent combinations can be used in the invention and are even contemplated herein. For example, if the filmogenic protein is transferrin, the bioactive agent could be any transferrin binding pharmacologic.

In all the following examples, all parts and percentages are by weight unless otherwise mentioned, all dilutions are by volume.

EXAMPLE 1

Phosphorothioate Oligonucleotide Synthesis

Chain extension syntheses were performed on a 1 μmole column support on an ABI Model 391 DNA synthesizer (Perkin Elmer, Foster City, Calif.) or provided by Lynx Therapeutics, Inc. (Hayward Calif.). The 1 micromole synthesis employed cyanoethyl phosphoroamidites and sulfurization with tetraethylthiuram disulfide as per ABI user Bulletin 58.

Radiolabeled oligonucleotides were synthesized as hydrogen phosphonate material by Glen Research (Bethesda, Md.). The uniformly $^{35}$S-labeled PS-ODN with sequences 5'-TAT GCT GTG CCG GGG TCT TCG GGC 3' (24-mer complementary to c-myb) (SEQ ID NO:2) and 5' TTAGGG 3' (SEQ ID NO:3) were incubated in a final volume of 0.5 ml with the perfluorocarbon-exposed sonicated dextrose albumin microbubble solution for 30 minutes at 37° C. The solutions were allowed to stand so that the bubbles could rise to the top and 100 microliters were removed from the clear solution at the bottom and 100 microliters were removed from the top containing the microbubbles.

Preparation of Microbubble Agent

Five percent human serum albumin and five percent dextrose were obtained from a commercial source. Three parts of 5% dextrose and one part 5% human serum albumin (total 16 milliliters) were drawn into a 35-milliliter Monojet syringe. Each dextrose albumin sample was hand agitated with 8±2 milliliters of either a fluorocarbon gas (decafluorobutane; molecular weight 238 grams/mole) or 8±2 milliliters of room air, and the sample was then exposed to electromechanical sonication at 20 kilohertz for 80±5 seconds. The mean size of four consecutive samples of the perfluorocarbon-exposed sonicated dextrose albumin (PESDA) microbubbles produced in this manner, as measured with hemocytometry was 4.6±0.4 microns, and mean concentration, as measured by a Coulter counter was 1.4× 10$^9$ bubbles/milliliter. The solution of microbubbles was then washed in a 1000 times volume excess of 5% dextrose to remove albumin which was not associated with the microbubbles. The microbubbles were allowed four hours to rise. The lower solution was then removed leaving the washed foam. The washed foam was then mixed with 0.9% sodium chloride.

Binding Assays

The radioactive 24-mer PS-ODN was added to a washed solution of PESDA and room air sonicated dextrose albumin (RA-SDA) microbubbles at a concentration of 5 nM. Non-radioactive PS-ODN 20-mer was added to tubes containing radioactive 24-mer in a series of increasing concentrations (0, 3.3, 10, 32.7, 94.5, 167, and 626 μM). The suspension of bubbles is mixed by inversion and incubated at 37° C. for 60 minutes.

Measurement of Radioactivity

Radioactivity in solutions were determined by liquid scintillation counting in a liquid scintillation counter (model LSC7500; Beckman Instruments GmbH, Munich, Germany). The sample volume was 100 μl to which 5 ml of Hydrocount biodegradable scintillation cocktail was added and mixed. Samples were counted immediately after each experiment and then again 24 hours later in order to reduce the influence of chemiluminescence and of quenching.

Flow Cytometry

The uniformity of room air versus perfluorocarbon-containing sonicated dextrose albumin microbubble binding of PS-ODN was determined by flow cytometry. A solution of microbubbles was washed in a 1000 fold excess volume of sterile saline. Three groups of samples were prepared in triplicate as follows; Group A (control) in which 100 μl of microbubbles were added to a 900 μL of saline, Group B in which 100 μ/l of microbubbles were added to 900 μL of saline and 2 μL of FITC-labeled 20-mer was added (final 20-mer concentration is 151 nM), and group C in which 100 μL of microbubbles were added to 800 μL of saline, 2 μL of FITC-labeled 20-mer and 100 μL of unlabeled 20-mer (final concentration is 151 nM). The incubations were all conducted for 20 minutes at room temperature.

Washed microbubble suspensions were diluted in sterile saline (Baxter) and then incubated with FITC-labeled PS-ODN. Flow cytometric analysis was performed using a FACStar Plus (Becton Dickinson) equipped with t 100 mW air-cooled argon laser and the Lysis II acquisition and analysis software. List mode data were employed for a minimum of 10$^4$ collected microbubbles and independent analysis a for each sample.

Study Protocol

A variable flow microsphere scanning chamber was developed for the study which is similar to that we have described previously Mor-Avi V., et al "Stability of Albunex microspheres under ultrasonic irradiation; and in vitro study. J Am Soc Echocardiology 7:S29, 1994. This system consists of a circular scanning chamber connected to a Masterflex flow system (Microgon, Inc., Laguna Hills Calif.) The scanning chamber was enclosed on each side by water-filled chambers and bound on each side by acoustically transparent material. The PS-ODN-labeled PESDA microbubbles (0.1 milliliters) were injected as a bolus over one second proximal to the scanning chamber which then flowed through plastic tubing into a tap water-filled scanning chamber at a controlled flow rate of 100 ml/min. As the bubbles passed through the scanning chamber, the scanner (2.0 Megahertz) frequency, 1.2 Megapascals peak negative pressure) was set to either deliver ultrasound at a conventional 30 Hertz frame rate or was shut off. Following passage through the scanning chamber, the solution was then passed through the same size plastic tubing into a graduated cylinder. The first 10 milliliters was discarded. Following this, the next 10 milliliters was allowed to enter into a collection tube. The collection tube containing the effluent microbubbles was allowed to stand in order to separate microbubbles on the top from whatever free oligonucleotide existed in the lower portion of the sample. Drops from both the upper and lower operation of the effluent were then placed upon a hemocytometer slide and analyzed using a 10× magnification. Photographs of these slides were then made and the number of microbubbles over a 36 square centimeter field were then hand-counted. The upper and lower layers of the remaining effluent were then used for analysis of oligonucleotide content using flow cytometry in the same manner described below.

Microbubble samples exposed to the various oligonucleotide solution were mixed 15 (v/v) with a solution of formamide and EDTA and heated to 95° C. for 5 minutes. These samples were then examined on an Applied Biosystems Model 373A DNA sequencer with e 20% polyacrylamide gel. The data were acquired with GeneScanner software so that fluorescence intensity area under the curve could be determined.

EXAMPLE 2

Phosphorothioate Oligonucleotide Binding of PESDA versus RA-SDA Microbubbles

The partitioning of PS-ODN to PESDA microbubbles top layer) and non-bubble washed (albumin-free) and unwashed (non-bubble albumin containing) lower layers as counted by liquid scintillation counting are demonstrated in Table 1.

TABLE 1

OLIGONUCLEOTIDES BINDING TO
ALBUMIN OF PESDA MICROBUBBLES

|  | N | TOP cpm/µl | BOTTOM cpm/µl | RATIO T/B |
|---|---|---|---|---|
| BUBBLES IN THE PRESENCE OF FREE ALBUMIN ||||
| TTAGGG | 6 | 125 ± 6.4 | 92.3 ± 6.4 | 1.35 |
| c-myb | 6 | 94.1 ± 17.6 | 77.3 ± 1.2 | 1.35 |
| WASHED BUBBLES (NO FREE ALBUMIN) ||||
| TTAGGG | 6 | 210 ± 10.8 | 126 ± 8.7 | 1.67 |
| c-myb | 6 | 200.3 ± 37.4 | 92.7 ± 15.7 | 2.16 |

These data indicate that albumin in the unwashed solution which is not associated with the microbubble will bind to the PS-ODN so that the partitioning of PS-ODN is equivalent between microbubbles (top layer) and the surrounding solution (lower layer; p=HS). Removal of non-microbubble associated albumin (Washed Bubbles in Table 1) does not show a significant partitioning of the PS-ODNs with the PESDA microbubbles (1.67 for TTAGGG PS-ODN and 2.16 for c-myb PS-ODN). The recovery of total radioactivity in the experiments reported in Table 1 is 96% of the radioactivity added which is not significantly different from 100%.

Figure 1:
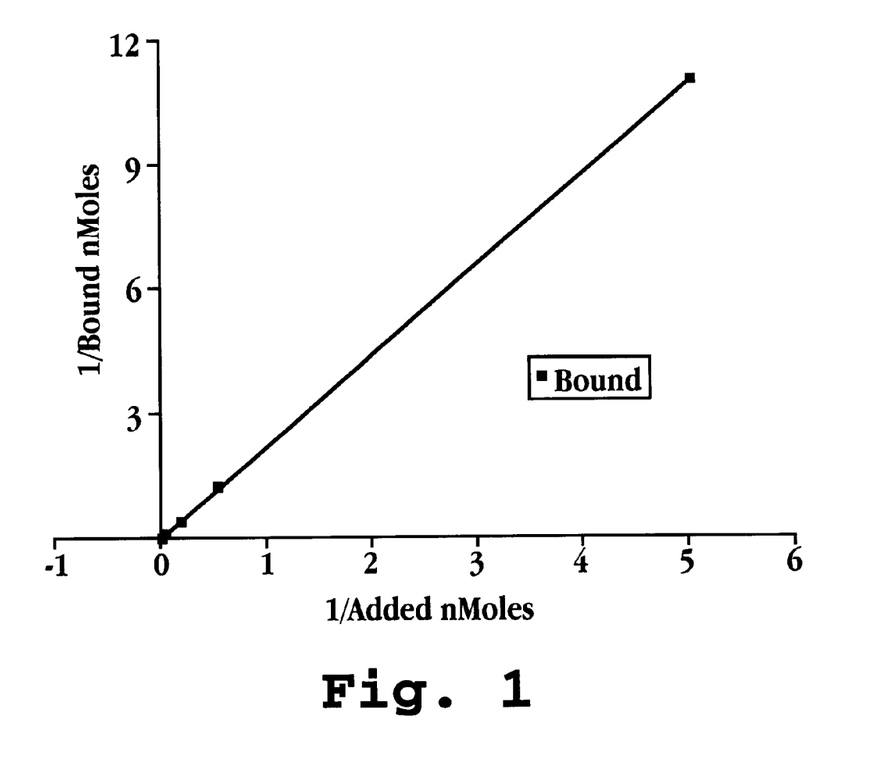

The affinity of binding of PS-ODN to washed microbubbles was evaluated by addition of increasing amounts of excess non-radioactive PS=ODN as a competing ligand for binding sites. In this case a 20mer PS-ODN with sequence 5'-d(CCC TGC TCC CCC CTG GCT CC)-3' (SEQ ID NO:4) was employed to displace the radioactive 24mer. Albumin protein concentrations in the washed microbubble experiments was 0.28±0.04 mg/ml as determined by the Bradford Assay Bradford M et al "A Rapid and Sensitive Method for the quantification of microgram quantities of protein utilizing the principle of protein-dye binding" anal. Bioche,. 72:248, 1976. The observed binding data are presented as a Lineweaver Burke plot in FIG. 1. The equilibrium dissociation constant $K_m$ (calculated for the 7 concentrations which were run in duplicate) for the binding to the microbubbles was $1.76 \times 10^{-5}$ M.

The distribution of FITC-labeled microbubbles is provided in Table 2.

TABLE 2

DISTRIBUTION OF OLIGONUCLEOTIDE (PS-ODN) BOUND MICROBUBBLES

|  | Control PS-ODN || 151 nM FITC PS-ODN || Excess Unlabeled ODN ||
| No. | PE | MI | PE | MI | PE | MI |
|---|---|---|---|---|---|---|
| 1 | 99.5 | 2.38 | 98.9 | 2109.8 | 97.8 | 1753.1 |
| 2 | 99.3 | 4.07 | 99.1 | 2142.3 | 98.7 | 1710.9 |
| 3 | 99.4 | 3.52 | 99.1 | 2258.5 | 99.3 | 1832.2 |
| mean ± SE |  | 3.23 ± 0.50 |  | 2170 ± 46[1] |  | 1765 ± 36[1,2] |

PE = percent events
MI = mean intensity
SE = standard error
[1]indicates this mean is significantly different form control, P < 0.001
[2]indicates this mean is significantly different form 151 nM, P < 0.001

The significant decrease in mean fluorescence intensity in the samples containing excess unlabeled PS-ODN indicates the binding to microbubbles is saturable. Consequently, since the binding is saturable, the nonspecific interactions of PS-ODN with the microbubble surface are limited. A Gaussian distribution of PS-ODN to washed PESDA microbubbles indicated that the albumin on these microbubbles had retained its binding site for the oligonucleotide. The absence of a Gaussian distribution for washed RA-SDA indicated loss of albumin binding site 1 for this oligonucleotide occurred during sonication of these microbubbles. For a discussion of albumin binding characteristics particularly as they relate to oligonucleotides see Kumar, Shashi et al "Characterization of Binding Sites, Extent of Binding, and Drug Interactions of Oligonucleotides with Albumin" Antisense Research and Development 5: 131–139 (1995) the disclosure of which is hereby incorporated by reference.

From the foregoing it can be seen that, PS-ODN binds to the albumin in PESDA microbubbles, indicating that the binding site 1 on albumin is biologically active following production of these bubbles by electromechanical sonication. This binding site affinity is lost when the electromechanical sonication is performed only with room sir. Further, removal of albumin not associated with PESDA microbubbles by washing shows a significant partitioning of the PS-ODNs with the microbubbles (Table 1). These observations demonstrate that albumin denaturation does not occur with perfluorocarbon-containing dextrose albumin solutions during sonication as has been suggested with sonication in the presence of air. The retained bioactivity of albumin (especially at site 1) in PESDA microbubbles was confirmed by the affinity of binding of PS-ODN to washed PESDA microbubbles in the presence of increasing amounts of excess non-radioactive PS-ODN as a competing ligand for binding sites (Table 2). The significant decrease in mean fluorescence intensity in the samples containing excess unlabeled PS=–ODN indicates the binding to microbubbles is saturable.

EXAMPLE 3

Altered Biodistribution Via Microbubble Delivery of Antisense Oligos

According to the invention antisense phosphorothioate oligonucleotides were designed to the cytochrome P450 IIB1 gene sequence to alter the metabolism of Phenobarbital. The oligonucleotides were conjugated to perfluoropropane exposed sonicated dextrose albumin microbubbles (PESDA) as earlier described and delivered to rats intravenously. The oligonucleotide was synthesized according to the rat cytochrome P450 IIB1 known sequence and had the following sequence:

GGAGCAAGATACTGGGCTCCAT (SEQ ID NO:5)

AAAGAAGAGAGAGAGCAGGGAG (SEQ ID NO:6)

Male Sprague-Dawley rats (Sasco, Omaha), were used and weighed between 210 to 290 grams for all studies. They were housed in animal quarters at the University of Nebraska Medical Center, AAALAC approved animal resource facility. The animals were exposed to 12 hour light/dark cycle and allowed access to Purina rat chow and tap water ad libitum.

Rats in groups with PB were injected intraperitoneally with phenobarbital (Mallinckrodt, St. Louis) at 80 ml/kg/day×2 days. The PB injections were given simultaneously with the ODN-microbubble injections. Phosphorothioate ODN injections were 1 ml/kg/day×2 days. Sleep times were measured 48 hours after the first injection. The rats were injected intraperitoneally with 100 ml/kg hexobarbital (Sigma, St. Louis), paired fresh daily. The volume of this injection is 1 ml/kg body weight.

Each rat was injected with 100 mg/kg of hexobarbital intraperitoneally. The animals were placed on their backs to insure that they were still under sedation from the hexobarbital. Sleep time is defined as the time they are placed on their backs to the time when they roll over. The sleep times listed are the mean of each animal in the group±standard deviation.

Results indicate that delivery of the oligonucleotide conjugated microbubbles greatly improved efficacy of the drug. Rats given ½₀th dose of oligo experienced a sleep time of more than 50 minutes. This is compared to non microbubble conjugated oligo with an approximate sleep time of 13 minutes Rats were ultimately sacrificed using ethyl ether and microsomes were prepared as described by Franklin and Estabrook (1971). Livers were perfused with 12 ml of 4% saline via the portal vein and then removed from the animal. The livers were minced, homogenized in 0.25 M sucrose (Sigma) and centrifuged at 8000×g for 20 minutes at 4° C. in a Sorvall RC2-B centrifuge (Dupont, Wilmington, Del.). The supernatant was saved and resuspended in a 0.25 M sucrose and centrifuged at 100,000×g for 45 minutes at 4° C. in a Sorvall OTD55B ultracentrifuge (Dupont). The pellet was resuspended in 1.15% KCL (Sigma) and centrifuged at 100,000×g for 1 hour at 4° C. with the final pellet resuspended in an equal volume buffer (10 mM Tris-acetate, 1 mM EDTA, 20% glycerol; Sigma) and frozen at −80° C.

Protein concentrations were determined by Bradford assay (Bradford, 1976). 80 µl aliquots of homogenate were added to a 96 well plate (Becton, Dickinson Labware, Lincoln Park, N.J.). 20 µl of Bradford reagent (Bio-Rad Richmond, Calif.) was then added and the plates read at 595 nm on the microplate reader (Molecular Devices, Newport Minn.). The data was compared to standard curve generated with known concentrations of bovine serum albumin (Sigma).

CYP IIB1 content was determined by pentoxyresorufin O-dealkylation (PROD) activity (Burke et al. 1985). For each microsomal sample, 1 mg protein in 1 ml 0.1 M potassium phosphate buffer, 1 ml 2 µM 5-pentoxyresorufin (Pierce, Rockford, Ill.), and 17 µl 60 mM NADPH were mixed and incubated for 10 minutes at 37° C. The mixture was then added to a 2 ml cuvette and read on a RF5000U spectrofluorophotometer (Shimadzu, Columbia, Md.) using an excitation wavelength of 530 nm and emission wavelength of 585 nm. Concentrations of unknowns were calculated from a standard curve of resorufin (Pierce, Rockford, Ill.) standards. Results were recorded in nmol resorufin/mg protein/min.

Direct measurement of CYP IIB1 protein was determined by an ELISA assay using an antibody directed the CYP IIB1 protein (Schuurs and Van Weeman, 1977). 50 µg of liver per well were plated in 100 µl 0.35% sodium bicarbonate buffer overnight on a 96 well nunc-immuno plate (InterMed, Skokie, Ill.). The microsomes were washed 3× with 1% bovine serum albumin in PBS (PBS/BSA) and incubated for 1 hr at 37° C. with 200 µl PBS/BSA. The PBS/BSA was removed and 50 µl of CYP IIB1 antibody (Oxygene, Dallas) was added and incubated for 1 hour at 37° C. The microsomes were washed 5× with saline/tween 20 (Sigma) and had 50 µl horseradish peroxidase antibody (Bio-rad) added. The microsomes were incubated for 1 hour at 37° C., washed 5× with saline/tween 20 and twice with 85% saline. 100 µl of horseradish peroxidase substrate (Kirkegaard & Perry Labs, Gaithersburg, Md.) was added and the plate read continuously in a microplate reader (Molecular Devices) at 405 nm for 1 hour. Results were recorded as horseradish peroxidase activity in mOD/min.

Results demonstrated that the oligo conjugated microbubbles directed the oligo to the liver and kidney. These are site of phenobarbitol metabolism. As described earlier, 100 mg/kg HB was injected i.p. to each animal at the end of 2 days of treatment with PB and/or the ODNs. Control rats had a sleep time of about 23 minutes. PB had a significant reduction in sleep time to about 11.4±4.5 minutes. PB stimulates CYP IIB1 mRNA, as a result, hexobarbital which is hydroxylated by CYP IIB1 is more quickly metabolized and its sedative effect reduced.

EXAMPLE 4

Comparison Study of Microbubbles Formed in Nitrogen-Free Versus Room Air Environments The perfluorocarbon containing microbubbles (PCMB) used for this study were perfluorocarbon exposed sonicated dextrose albumin. To prepare these microbubbles, one part 5% human serum albumin and three parts 5% dextrose (total of 16 ml) were combined in a 35 ml Monoject syringe (Sherwood Medical, St. Louis, Mo.). This sample was then hand-agitated with 8 ml of fluorocarbon gas (decafluorobutane; MW 238 g/mol). Following the agitation, the sample underwent electromechanical sonication for 80±2 seconds.

For in vivo studies, the 80 second sonication process was performed in two different environments: either room air or 100% oxygen (nitrogen-free environment) was blown into the interface between the sonicating horn and perfluorocarbon dextrose albumin solution during sonication. Each of the samples prepared in this manner had microbubble size determined with hemocytometry and concentration determined with a Coulter counter (Coulter Electronics, Inc. Hiahleah, Fla.).

In Vitro Scanning Chamber Set Up

The scanning chamber system consisted of a 35 ml cylindrical scanning chamber connected to a peristaltic Masterflex flow system (Microgon, Inc., Laguna Hills, Calif.). Enclosed on both sides of the scanning chamber are cylindrical saline filled chambers, bound by acoustically transparent latex material that is 6.6 microns in thickness (Safeskin, Inc.; Boca Raton, Fla.). Pressure within the scanning chamber during ultrasound exposure was measured with a pressure transducer placed just proximal to the scanning chamber (model 78304A; Hewlett Packard Co., Andover, Mass.), and averaged 7±3 mm Hg throughout all of the trials.

Two different 2.0 Megahertz ultrasound transducers were used for the in vitro studies (Hewlett Packard 1500; Andover, Mass.; and HDI 3000, Advanced Technology Laboratories, Bothell, Wash.). The peak negative pressure generated by the Hewlett Packard transducer was 1.1 megapascals, while it was 0.9 megapascals for the HDI 3000 scanner. Imaging depth for all studies was 8.2 centimeters, and the focal point for both transducers was 8 centimeters. The frame rate for each transducer was either conventional (30–42 Hertz) or intermittent (1 Hertz). All images from the scanning chamber were recorded on high fidelity videotape.

In Vitro Protocol

Arterial blood during room air inhalation was taken from four dogs and three healthy pigs just prior to sacrifice. In four of the animals, additional arterial blood was obtained after the animal had inhaled 100% oxygen for a minimum of 10 minutes. The blood was collected in 60 ml heparinized syringes, and kept in a warm water bath at 37° C. until injected into the scanning chamber. Immediately before injection of the blood into the scanning chamber, 0.2 ml of PCMB were injected via a stopcock into the 60 ml syringe of blood, and mixed gently by inverting and rolling the syringe by hand.

Once the PCMB were well-mixed with the blood, the tip cap was removed from the syringe, and the syringe was connected to plastic tubing (3.5 mm in diameter) proximal to the Masterflex flow system. At a flow rate of 50 ml/minute, the contrast filled blood flowed from the syringe into the tubing and then into the scanning chamber. Once the chamber was filled, the closed stopcock connecting the scanning chamber to the plastic tubing distal to the chamber was opened, and ultrasound exposure (intermittent at 1 Hertz frame rate or conventional at 30–45 Hertz) was initiated. The effluent blood after ultrasound exposure flowed out of the scanning chamber into tubing which was connected to a graduated cylinder. The first 10 ml of blood was discarded, and the next 15 ml of blood that flowed from the chamber was collected in three 5 ml aliquots into inverted capped syringes. Three minutes following the collection of the last 5 ml sample, a tuberculin syringe was dipped into the top level of the effluent blood and a drop placed on a hemocytometer slide; this length of time was chose to allow the microbubbles in the effluent blood to rise to the top and be collected. The hemocytometer slide was then examined at 40× magnification with a light microscope (Olympus BH-2, Olympus America Inc., Woodbury, N.Y.) and the field containing the highest concentration of microbubbles was photographed on the hemocytometer field.

The photos were later enlarged on a photocopy machine, and a 25 $cm^2$ field was chosen to analyze concentration and the diameter of each microbubble in the field. The mean diameter was calculated, thus giving mean microbubble size. Concentration was determined by counting the total number of bubbles in the entire slide. Microbubble concentration measured with this technique has correlated very closely with Coulter counter measurements, and size measurements with this technique have been calibrated with a known 5 micron sphere (Coulter Size Standards Nominal 5 $\mu$m Microspheres, Miami, Fla.).

In Vivo Studies

The inventors subsequently tested the effect of a nitrogen-free environment within the perfluorocarbon microbubble by randomly giving intravenous injections of PCMB of the same concentration of microbubbles exposed to either 100% oxygen (O2 PCMB) or room air (RA PCMB) during sonication. Imaging was performed with a 1.7 megahertz harmonic transducer (HDI 3000; Advanced Technology Laboratories; Bothell, Wash.). Transducer output was set to 0.3–0.8 megapascals, and kept constant for all comparisons of videointensity from the two different microbubble samples. Frame rates for comparison of background subtracted myocardial videointensity were either 43 Hertz (conventional) or 10 Hertz (intermittent). All procedures were approved by the Institutional Animal Care and Use Committee and was in compliance with the Position of the American Heart Association on Research Animal Use.

The bolus injections of RA PCMB and O2 PCMB were either 0.0025 or 0.005 ml/kg, since the concentrations of each microbubble were the same. Peak anterior and posterior myocardial videointensity were measured from digitized super VHS videotape images (Maxell, Japan) obtained off-line using a Tom-Tech review station (Louisville, Colo.). This quantifies videointensity over a 1–255 gray scale range. The region of interest was placed in the mid myocardium of each segment.

In addition to this quantitative analysis, the visual assessment of regional myocardial contrast enhancement in the anterior, septal, lateral, and posterior regions from the short axis view was made by two independent reviewers. Each region was assigned a 0 (no myocardial contrast), 1+ (mild myocardial contrast enhancement) or 2+ (bright myocardial contrast enhancement which approached cavity intensity).

Statistical Analysis

An unpaired t test was used to compare microbubble size and concentration of the PCMB samples exposed to different gases during sonications. This was also used to compare differences in peak myocardial videointensity in the in vivo studies. If the data was not normally distributed, a non-parametric test was performed. Comparisons of visual myocardial contrast enhancement following intravenous O2 PCMB and RA PCMB were made with continency tables (Fisher's Exact Test). A p value less than 0.05 was considered significant.

A coefficient of variation was used to measure interobserver variability in the measurements of microbubble size and concentration in the in vitro studies. A mean difference between independent reviewers was used to compare interobserver variations in peak myocardial videointensity.

Results

Table 3 demonstrates differences in mean microbubble size for PCMB after exposure to ultrasound in arterial blood (room air and 100% oxygen). When PCMB were exposed to 100% oxygenated arterial blood, there was a significant decrease in mean microbubble size after insonation ($p=0.01$). The smaller microbubble size was seen both after intermittent imaging (7.3±3.7 microns room air vs. 6.4±3.2 microns 100% oxygen) and after conventional imaging (7.5±3.5 microns room air vs. 6.3±3.0 microns 100% oxygen).

Microbubble concentration decreased significantly after exposure to conventional frame rates when compared to intermittent imaging in room air arterial blood (Table 3). However, conventional frame rates at the same transducer output did not destroy as many PCMB when they were in oxygenated arterial blood.

TABLE 3

COMPARISON OF EFFLUENT PESDA MICROBUBBLE SIZE AFTER EXPOSURE TO DIFFERENT ULTRASOUND FRAME RATES IN ROOM AIR AND 100% OXYGENATED ARTERIAL BLOOD

|  | MB size | MB Conc. (No./hpf) | |
| --- | --- | --- | --- |
|  | ($\mu$m) | Conv | Inter |
| Arterial | 7.4 ± 3.6 | 6 ± 8 | 16 ± 11† |
| Arterial +O$_2$ | 6.3 ± 3.1 | 11 ± 9 | 14 ± 9* |

Conv = Conventional frame rates (80 to 43 Hz)
No./hpf = Number of microbubbles per high-power field
MB = microbubble
Inter = Intermittent imaging at 1 Hz
*$p < 0.05$ r test compared with arterial samples
†$p < 0.05$ compared with arterial conv.

In Vivo Studies

A total of six comparisons of peak myocardial videointensity between O$_2$ PCMB and RA PCMB were made in the three dogs. In Table 4, it can be seen that prior to injection, the PCMB sonicated in the presence of 100% oxygen were similar in size and concentration to PCMB sonicated in the presence of room air. However, in all three dogs, the peak myocardial videointensity using the 10 Hertz frame rate (intermittent imaging) was significantly higher for the PCMB sonicated in the presence of 100% oxygen.

Only the oxygenated PCMB produced a consistent homogenous myocardial contrast at the doses used for transthoracic imaging. Visual myocardial contrast was 2+ in 20 of the 24 regions following intravenous O$_2$ PCMB injections compared to 9 or 24 regions following the same dose of RA PCMB ($p=0.001$).

TABLE 4

COMPARISON OF PMVI PRODUCED IN ANTERIOR AND POSTERIOR WALL OF LEFT VENTRICULAR SHORT-AXIS VIEW AT MID PAPILLARY MUSCLE LEVEL AFTER INTRAVENOUS VEIN INJECTION OF PCMB SONICATED IN THE PRESENCE OF 100% OXYGEN AND ROOM AIR

|  | PMVI (units) | | Microbubble | |
| --- | --- | --- | --- | --- |
|  | Ant | Post | Size ($\mu$m) | Conc (No./hpf) |
| RA PCMB | 54 ± 12 | 19 ± 9 | 4.0 ± 2.4 | 109 ± 30 |
| O$_2$ PCMB | 70 ± 6* | 31 ± 5* | 3.9 ± 2.3 | 108 ± 50 |

Ant = anterior myocardium
Conc = microbubble concentration immediately after sonication
O$_2$ PCMB = perfluorocarbon microbubbles sonicated in the presence of 100% oxygen
PMVI = peak myocardial videointensity
Post = posterior myocardium
RA PCMB = perfluorocarbon microbubbles sonicated in the presence of room air
No./hpf = number of microbubbles per high-power field
*$p < 0.05$ compared with RA PCMB Interobserver Variability in Microbubble Size, Concentration, and Videointensity Measurements Two independent observers measured microbubble size and concentration of six different slides exposed to either intermittent or conventional ultrasound frame rates. The coefficient of variation for measurements of microbubble size by two independent observers in six different samples was 8% ($r=0.95$; $p=0.004$), while the coefficient of variation for independent measurements of microbubble concentration was 9% ($r=0.99$; $p<0.001$). The reported mean difference in peak myocardial videointensity measurements by two independent reviewers for transthoracic imaging is 4±4 units ($r=0.94$, SEE=5 units; $p<0.001$; $n=24$ comparisons), which is well below the 16 unit mean difference in anterior and 13 unit mean difference in posterior peak myocardial videointensity between O2 PCMB and RA PCMB. The two investigators were in agreement of the visual degree of contrast enhancement in 37 of the 44 regions (84%). Five of the discrepancies were in visual grading of RA PCMB myocardial contrast enhancement (0 vs 1+ in two regions, 1+ vs. 2+ in three regions). The three regions where there was disagreement on whether there was 1+ vs 2+ were assigned a 2+ in the statistical analysis.

Microbubbles containing an albumin shell such as the one used in this study permit rapid diffusion of soluble gases across their membranes. Perfluorocarbon containing microbubbles survive longer than room air containing microbubbles with the same membrane because of the slow rate of diffusion of this higher molecular weight gas and its insolubility in blood. These microbubbles, however, still contain a significant quantity of room air gas and thus are not affected by the concentration gradient that exists across the albumin membrane. Since surface tension and absorptive pressures are increased as microbubble diameter decreases, it was hypothesized that the videointensity produced by intravenous PCMB would also be affected by alterations in nitrogen and oxygen concentration inside and outside the microbubble.

The in vitro studies confirmed that oxygenated blood reduced PCMB size but did not completely destroy them as has been shown with pure room air containing albumin microbubbles. Wible J. Jr., et al. (1993), Effects of inspired gas on the efficacy of Albunex® in dogs. Circulation 88(suppl):1–401. Abstract. To counter this process, the inventors attempted to reverse this diffusion gradient by removing nitrogen within the microbubbles. It was hypothesized that this would have the opposite effect of that seen with oxygenated blood, resulting in nitrogen diffusion inward. The in vitro and in vivo findings of this study appear to support this hypothesis.

PESDA Microbubble Concentration and Size in Arterial Blood: In Vitro Studies

It has previously been shown that PCMB diameter increases after initial exposure to blood at 37° C., most likely from gas expansion from room temperature to body temperature. Although this explains why microbubble size increased in all samples tested, the PCMB exposed to 100% oxygenated arterial blood were significantly smaller in size compared to PCMB exposed to room air blood (Table 3). This observation was seen both following intermittent and conventional imaging. Without wishing to be bound by any theory, it is postulated the one potential explanation for this is the differences in nitrogen diffusion gradients across the microbubble membrane. Since all PCMB in the in vitro study were sonicated in the presence of room air, there was a significant quantity of nitrogen within the microbubble. Mathematical models have suggested that microbubbles containing insoluble gases persist longer if tissue and blood contain nitrogen. (Burkard 1994). In the absence of blood nitrogen (i.e.: 100% oxygenated blood), nitrogen from within the PCMB would have diffused out of the PCMB, reducing their size.

As expected, microbubble concentrations in room air blood were significantly reduced when exposed to higher frame rates. However, this destruction by more rapid frame rates was attenuated somewhat when the PCMB were in oxygenated blood. The reason for this difference is unclear. One possibility is that the more rapid diffusion of nitrogen out of the microbubbles in oxygenated blood created a higher internal concentration of perfluorocarbon, and thus increased the diffusion gradient for the insoluble perfluorocarbon. Due to its low solubility, its enhanced diffusion out of the microbubble would lead to the formation of smaller unencapsulated perfluorocarbon microbubbles. The hemocytometry resolution would be unable to differentiate encapsulated from unencapsulated microbubbles and thus would count them both. This explanation may also account for the smaller mean microbubble size observed for PCMB exposed to 100% oxygenated arterial blood.

PCMB Sonicated in a Nitrogen-Free Environment: In Vivo Demonstration of Improved Efficacy Over PCMB Sonicated in the Presence of Room Air Based on the in vitro studies, whether the detrimental effects of a high external oxygen content could be utilized to an advantage by lowering nitrogen content within the PCMB was examined. This was accomplished in our study by sonicating the PCMB in the presence of 100% oxygen. Since perfluorocarbons like decafluorobutane act as a mechanical stabilizer, it was hypothesized that this would create an environment where nitrogen diffuses inward following venous injection, further enhancing the stability of the PCMB in blood. This was consistently effective in the closed chest studies in creating greater myocardial contrast than PCMB sonicated in the presence of room air. Even with intermittent imaging using pulsing intervals as short as 100 milliseconds (10 Hertz imaging), visually evident myocardial contrast was still achieved with the microbubbles sonicated in a nitrogen-free environment.

What is claimed is:

1. A microbubble composition useful for ultrasonic imaging or for delivery of a biological agent to a target site, comprising: an aqueous suspension comprising a plurality of protein encapsulated insoluble gas-containing microbubbles, wherein said microbubbles have an enhanced oxygen content and a decreased partial pressure of nitrogen compared to that of microbubbles formed by sonication in the presence of room air.

2. The composition of claim 1, wherein said protein is selected from the group consisting of albumin, human gamma globulin, human apotransferin, beta lactose and urease.

3. The composition of claim 1, wherein said protein is albumin.

4. The composition of claim 1, wherein said gas is a perfluorocarbon gas.

5. The composition of claim 1, wherein said gas is selected from the group consisting of perfluoromethane, perfluoroethane, perfluoropropane, perfluorobutane, and perfluoropentane.

6. The composition of claim 1, wherein said gas is perfluorobutane.

7. The composition of claim 1, wherein said gas is perfluoropropane.

8. The composition of claim 1, wherein said microbubbles are formed by sonication in the presence of 100% oxygen.

9. The composition of claim 8, wherein said microbubbles are formed by introducing said oxygen into the interface between a sonicating horn and an aqueous mixture of said protein and said insoluble gas.

* * * * *